US010398346B2

(12) United States Patent
Ghoraani et al.

(10) Patent No.: US 10,398,346 B2
(45) Date of Patent: Sep. 3, 2019

(54) SYSTEMS AND METHODS FOR LOCALIZING SIGNAL RESOURCES USING MULTI-POLE SENSORS

(71) Applicant: Florida Atlantic University, Boca Raton, FL (US)

(72) Inventors: Behnaz Ghoraani, Boca Raton, FL (US); Prasanth Ganesan, Boca Raton, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 88 days.

(21) Appl. No.: 15/595,110

(22) Filed: May 15, 2017

(65) Prior Publication Data
US 2018/0325418 A1   Nov. 15, 2018

(51) Int. Cl.
*A61B 5/00* (2006.01)
*A61B 5/06* (2006.01)
(Continued)

(52) U.S. Cl.
CPC ............ *A61B 5/061* (2013.01); *A61B 5/0422* (2013.01); *A61B 5/6852* (2013.01); *A61N 1/00* (2013.01); *A61B 5/743* (2013.01); *A61B 18/1492* (2013.01); *A61B 2018/00351* (2013.01); *A61B 2018/00357* (2013.01);
(Continued)

(58) Field of Classification Search
CPC ....... A61B 5/061; A61B 5/743; A61B 5/0422; A61B 5/04017; A61B 5/044; A61B 5/6852; A61B 5/0452; A61B 18/12
See application file for complete search history.

(56) References Cited

U.S. PATENT DOCUMENTS 5,741,214 A * 4/1998 Ouchi ................. A61B 5/0422
600/374
6,226,542 B1 * 5/2001 Reisfeld ............. A61B 5/04011
600/407
(Continued)

FOREIGN PATENT DOCUMENTS

WO    2013052944 A1    4/2013

OTHER PUBLICATIONS

International Search Report dated Aug. 24, 2018 in PCT/IB2018/053195.
(Continued)

*Primary Examiner* — Michael W Kahelin
*Assistant Examiner* — Sana Sahand
(74) *Attorney, Agent, or Firm* — Fox Rothschild LLP

(57) ABSTRACT

Systems and methods for guiding a sensor to locate a source of a propagating wave. The methods involve: presenting an electronic display comprising an image representing an object in which the sensor is placed and a visual indicator representing the sensor; receiving signals generated by electrodes while the sensor resides at a first location in the object; determining a First Recommended Direction of Travel ("FRDT") for the sensor based on the received signals; using the FRDT to generate a mask that is to cover at least a portion of the image representing a portion of the object that is absent of the source; and modifying the electronic display to include the mask overlaid on top of the image and an arrow showing FRDT.

21 Claims, 15 Drawing Sheets

(51) Int. Cl.
 A61B 5/042 (2006.01)
 A61N 1/00 (2006.01)
 A61B 18/00 (2006.01)
 A61B 18/14 (2006.01)

(52) U.S. Cl.
 CPC ........... *A61B 2018/00577* (2013.01); *A61B 2018/00839* (2013.01); *A61B 2018/00904* (2013.01)

(56) References Cited

U.S. PATENT DOCUMENTS

| | | | |
|---|---|---|---|
| 7,263,397 B2* | 8/2007 | Hauck | A61B 5/0422 600/374 |
| 2007/0021679 A1 | 1/2007 | Narayan et al. | |
| 2013/0116538 A1* | 5/2013 | Herzog | A61B 5/743 600/407 |
| 2013/0116681 A1* | 5/2013 | Zhang | A61B 18/1206 606/34 |
| 2013/0274582 A1* | 10/2013 | Afonso | A61B 5/0422 600/374 |
| 2014/0081114 A1* | 3/2014 | Shachar | A61B 5/6858 600/378 |
| 2015/0164356 A1 | 6/2015 | Merschon et al. | |
| 2015/0208942 A1* | 7/2015 | Bar-Tal | A61B 5/0422 600/374 |
| 2015/0289807 A1* | 10/2015 | Narayan | A61B 5/0422 600/508 |
| 2015/0327805 A1* | 11/2015 | Ben-Haim | A61B 6/037 600/411 |
| 2016/0100770 A1* | 4/2016 | Afonso | A61B 5/0422 600/515 |
| 2016/0183824 A1* | 6/2016 | Severino | A61B 5/044 600/523 |
| 2016/0183830 A1* | 6/2016 | Laughner | A61B 5/0432 600/374 |
| 2016/0331337 A1* | 11/2016 | Ben-Haim | A61B 6/503 |
| 2017/0086694 A1* | 3/2017 | Stewart | A61B 5/044 |
| 2017/0202472 A1* | 7/2017 | Zeidan | A61B 5/0422 |
| 2017/0281031 A1* | 10/2017 | Houben | A61B 5/0422 |
| 2017/0304644 A1 | 10/2017 | Kruecker et al. | |
| 2017/0332971 A1* | 11/2017 | MacNeil | A61B 5/02405 |

OTHER PUBLICATIONS

Narayan, S.M., et al., "Clinical Mapping Approach to Diagnose Electrical Rotors and Focal Impulse Sources for Human Atrial Fibrillation," Journal of Cardiovascular Electrophysiology, vol. 23, Issue 5, May 2012, ISSN: 1045-3873.

Narayan, S.M., et al., "Ablation of Rotor and Focal Sources Reduces Late Recurrence of Atrial Fibrillation Compared to Trigge Ablation Alone," Journal of the American College of Cardiology (2014), doi: 10/1016j.jacc.2014.02.543.

Ganesan, P., et al., "Characterization of Electrograms from Multipolar Diagnostic Catheters During Atrial Fibrillation," Hindawi Publishing Corporation, BioMed Research International, vol. 2015, Article ID 272954, copyright 2015.

Salmin, A.J., et al., A Novel Catheter-Guidance Algorithm for Localization of Atrial Fibrillation Rotor and Focal Sources, copyright 2016 IEEE, 978-1-4577-0220-4/16.

Ganesan, R., et al., "Development of a Novel Probabilistic Algorithm for Localization of Rotors during Atrial Fibrillation," copyright 2016 IEEE, 978-1-4577-0220-4/16.

Ganesan, P., et al., "Rotational Activities During Atrial Fibrillation Associate with Incremental Gradient of Total Conduction Delay from Multi-Polar Diagnostic Catheters," Rochester Institute of Technology, SUNY Upstate Medical University, BSIA Lab, Oct. 2014.

Salmin, A.J., et al., "An Algorithm to Guide Multi-Pole Diagnostic Catheters Towards an Atrial Fibrillation Sustaining Site," Rochester Institute of Technology, SUNY Upstate Medical University, Oct. 2015.

Salmin, A., et al., "An Algorithm to Guide Multi-Pole Diagnostic Catheters Towards an Atrial Fibrillation Sustaining Site," Rochester Institute of Technology, SUNY Upstate Medical University, Jan. 2016.

Salmin, A.J., et al., "Developing and Evaluating a Novel Tracking Algorithm to Guide Multi-Pole Diagnostic Catheters Towards Atrial Fibrillation Sites," University of Rochester Medical Center, Upstate Medical University, May 2016.

International Search Report dated Dec. 4, 2018 in in PCT/IB2018/055463.

* cited by examiner

Location L1

SYSTEMS AND METHODS FOR LOCALIZING SIGNAL RESOURCES USING MULTI-POLE SENSORS

STATEMENT REGARDING FEDERAL FUNDING

This invention was made with government support under contract number R15 HL127663 awarded by the National Institute of Health. The government has certain rights in the invention.

BACKGROUND

Statement of the Technical Field

The present disclosure concerns generally to computing devices. More particularly, the present invention relates to implementing systems and methods for localizing signal sources using multi-pole sensors.

Description of the Related Art

Atrial Fibrillation ("AF") is the most common heart rhythm disorder and affects 2.7 million Americans, accounting for frequent health care utilization, increased hospitalizations and increased risks of stroke, heart failure and mortality. Ectopic beats from the pulmonary veins may trigger AF, the discovery of which led to the development of a non-pharmacological ablation therapy called Pulmonary Vein ("PV") isolation, which uses radiofrequency energy to cauterize the atrial tissue in the PV's antrum in order to terminate AF and restore sinus rhythm. Unfortunately, this therapy remains suboptimal with long-term success rates of only 40% to 60%. One of the main reasons for such unsuccessful outcomes is that it fails to eliminate AF drivers outside the PVs, and their targeted elimination is key to improving outcome after AF ablation. Detection and ablation of the rotors or foci has a very significant impact on the successful termination of AF. In animal studies where AF is induced with acetylcholine and rapid pacing, optical phase mapping of action potentials has shown that rotors outside PVs are relevant to the perpetuation of AF and should be targeted for AF ablation. Similarly, in human studies, phase maps derived from basket catheter unipolar electrograms have been used to detect rotors and foci and ablate these sites. It has been shown that ablation of rotor AF sources along with PV isolation is more durable than standalone PV isolation at preventing AF recurrence at 3 year-follow up.

However, a recent method to location rotors is based on a 64-pole basket catheter and inherits the limitations of a basket catheter. For example, the resolution is limited to the proportion of electrodes in contact with endocardium and good electrode contact at all sites on the endocardium is difficult to ensure because of irregularities in the cardiac chamber surface, so that areas crucial to the arrhythmia circuit may not be recorded. Moreover, regions such as the left atrial appendage are incompletely covered by the basket catheter. As a result, the basket catheter does not record arrhythmia substrates involving these structures. Additionally, basket catheter mapping does not permit immediate correlation of activation times to precise anatomical sites, and a Multi-Polar Diagnostic Catheter ("MPDC") must still be manipulated to the identified site for more precise mapping and localization of the target for ablation, as well as for RF energy delivery. Basket catheters also have limited torque capabilities and limited maneuverability, which hamper correct placement, and they can abrade the endocardium.

SUMMARY

The present invention concerns implementing systems and methods for guiding a sensor to locate a source of a propagating wave. The methods comprise presenting, by a computing device, an electronic display. The electronic display comprises an image representing an object in which the sensor is placed and a visual indicator representing the sensor. The visual indicator is positioned on the image so as to show a first location in the object or space at which the sensor currently resides. The computing device receives a plurality of signals generated by a plurality of electrodes of the sensor while the sensor resides at the first location in the object or space. A first recommended direction of travel for the sensor is determined by the computing device based on the received signals and/or atrial anatomy. The computing device then uses the first recommended direction of travel for the sensor to generate a mask (or map) that is to cover at least a portion of the image representing a portion of the object that is absent of the source. The electronic display is modified to include the mask overlaid on top of the image and an arrow showing the first recommended direction of travel for the sensor. The mask may include, but is not limited to, a colored mask showing a probability of the source's presence in a given area of the object.

In some scenarios, the methods comprise: analyzing by the computing device the plurality of signals to identify a first electrode of the plurality of electrodes which was activated first by the propagating wave; and determining, by the computing device, the first recommended direction of travel for the sensor based on the position of the first electrode relative to a reference point on the sensor. The methods may also comprise: determining, by the computing device, a first recommended distance of travel for the sensor based on a remaining search area within the object; and selecting, by the computing device, a length of the arrow based on the first recommended distance of travel.

In those or other scenarios, the sensor comprises an MPDC. The propagating wave comprises a propagating wave of bioelectricity. The plurality of signals comprises electrogram signals. The object is an atria.

In those or other scenarios, the visual indicator comprises a first marking representing the reference point and second markings respectively representing the electrodes. Adjacent ones of the second markings have a spacing illustrative of a spacing of adjacent ones of the electrodes. The arrow starts at a center of the visual indicator, passes through the marking representing the first electrode, and extends away from the center of the visual indicator by an amount. This amount can reflect the first recommended distance of travel for the sensor.

The mask is generated by: drawing a line that passes through the center of the visual indicator, is angled ninety degrees relative to the arrow, and extends between first and second boundary lines of a space; and defining a mask area as comprising a portion of the space that extends from the line in a direction opposed from the direction of the arrow.

In those or yet other scenarios, the methods involve: computing a value by dividing a first signal characteristic by a second signal characteristic; and iteratively modifying the mask in accordance with sensor movement until the value exceeds a threshold value. The first signal characteristic can include, but is not limited to, a Total Conduction Delay ("TCD"). The second signal characteristic can include, but is not limited to, a Cycle Length ("CL"). Additionally or alternatively, the mask is iteratively modified in accordance with sensor movement until an unmasked area of the image is less than or equal to a threshold area.

BRIEF DESCRIPTION OF THE DRAWINGS

Embodiments will be described with reference to the following drawing figures, in which like numerals represent like items throughout the figures.

DETAILED DESCRIPTION

Figure 1:
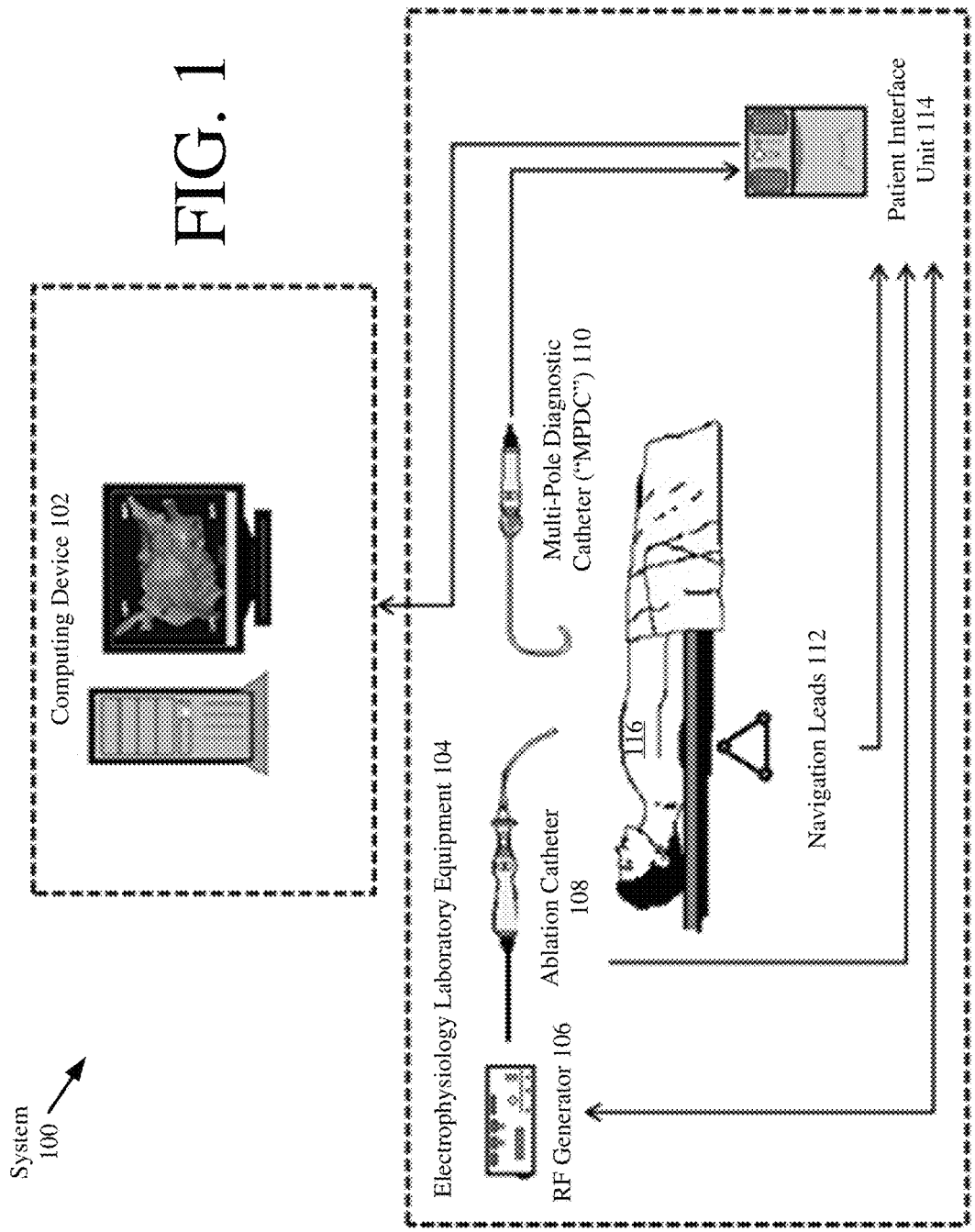
FIG. 1 is an illustration of an exemplary system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The present document generally concerns systems and methods for guiding an MPDC in an object (e.g., the atria of a subject) or space to develop a target map (e.g., an AF ablation target map), which reveals the location of any signal sources in the object or space. The present solution can be used in many applications. For example, the present solution can be used during an AF ablation procedure for successful detection and ablation of the AF sources (e.g., rotors or foci) outside the PVs and increasing the success of AF elimination procedures. The AF sources are sites with short cycle length, high dominant frequency, and/or high recurrence or similarity. Such AF sources include foci, rotors (spiral waves—meandering and non-meandering), scroll waves, and other arrhythmic source (e.g., AF, Atrial Tachycardia, Atrial Flutter, Ventricular Fibrillation, and/or Ventricular Tachycardia) this is in the form of a periodically/stably propagating wave without chaos. The present solution can be implemented in a computing device via hardware and/or software. In some scenarios, the present solution is implemented as a software add-on to the 3D mapping system in any of the existing AF mapping systems. Notably, the present solution is described below in relation to such an AF ablation procedure based scenario. However, the present solution is not limited in this regard. The present solution can be used in any application in which the source of a signal of interest is to be located through an iterative process.

Referring now to FIG. 1, there is provided an illustration of an exemplary system 100. System 100 is entirely or at least partially disposed within a facility, such as an electrophysiology laboratory. System 100 comprises a computing device 102 and electrophysiology laboratory equipment 104. The computing device 102 is configured to receive sensor information from the electrophysiology laboratory equipment 104. The sensor information can be acquired using a patient interface unit 114 and an MPDC 110. The ablation is performed using RF generator 106 and an ablation catheter 108. Each of the listed devices 106-110 is well known in the art, and therefore will not be described in detail herein. Any known or to be known RF generator, ablation catheter and/or MPDC can be used herein without limitation. The sensor information is communicated from the electrophysiology laboratory equipment 104 to the computing device 102 via a patient interface unit 114. The patient interface unit 114 performs any required processing necessary to allow the computing device 102 and laboratory equipment 114 to interoperate and communicate information therebetween.

The present solution is not limited to the hardware shown in FIG. 1. For example, any multi-polar catheter with reasonable resolution (electrode spacing) can be used without limitation. Such multi-polar catheters include, but are not limited to, a circular catheter, a catheter with branches, a spiral catheter, and/or an array catheter.

Figure 2:
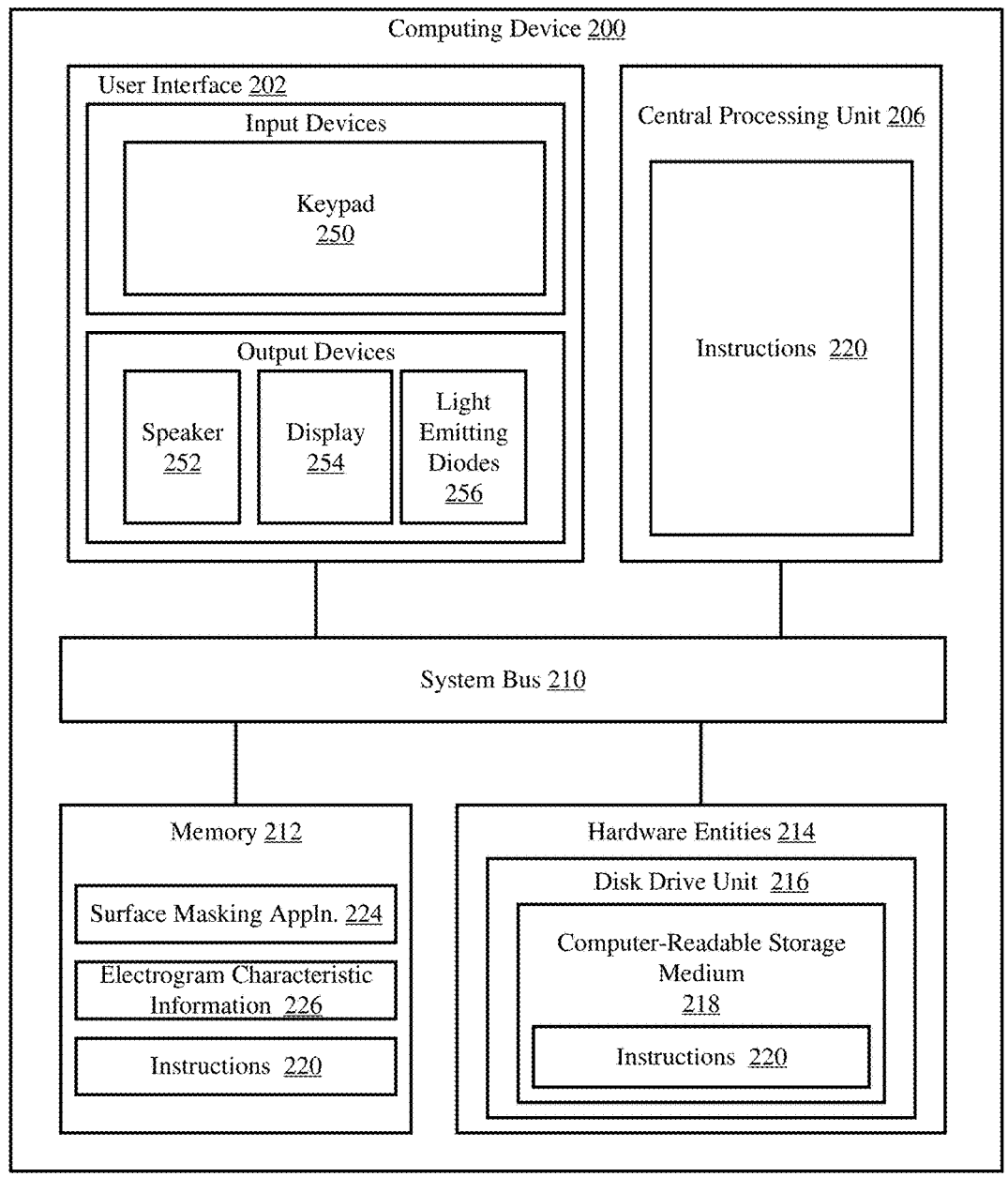
FIG. 2 is an illustration of an exemplary computing device.

Referring now to FIG. 2, there is provided a detailed block diagram of an exemplary architecture for a computing device 200. Computing device 102 of FIG. 1 is the same as or substantially similar to computing device 200. As such, the following discussion of computing device 200 is sufficient for understanding computing device 102.

Computing device 200 may include more or less components than those shown in FIG. 2. However, the components shown are sufficient to disclose an illustrative embodiment implementing the present solution. The hardware architecture of FIG. 2 represents one embodiment of a representative computing device configured to facilitate improved MPDC control and use. As such, the computing device 200 of FIG. 2 implements at least a portion of a method for automatically and dynamically guiding a sensing device (e.g., MPDC 110 of FIG. 1) to locate a signal source (e.g., an AF source) in accordance with the present solution.

Some or all the components of the computing device 200 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 2, the computing device 200 comprises a user interface 202, a Central Processing Unit ("CPU") 206, a system bus 210, a memory 212 connected to and accessible by other portions of computing device 200 through system bus 210, and hardware entities 214 connected to system bus 210. The user interface can include input devices (e.g., a keypad 250) and output devices (e.g., speaker 252, a display 254, and/or light emitting diodes 256), which facilitate user-software interactions for controlling operations of the computing device 200.

At least some of the hardware entities 214 perform actions involving access to and use of memory 212, which can be a RAM, a disk driver and/or a Compact Disc Read Only Memory ("CD-ROM"). Hardware entities 214 can include a disk drive unit 216 comprising a computer-readable storage medium 218 on which is stored one or more sets of instructions 220 (e.g., software code) configured to implement one or more of the methodologies, procedures, or functions described herein. The instructions 220 can also reside, completely or at least partially, within the memory 212 and/or within the CPU 206 during execution thereof by the computing device 200. The memory 212 and the CPU 206 also can constitute machine-readable media. The term "machine-readable media", as used here, refers to a single medium or multiple media (e.g., a centralized or distributed database, and/or associated caches and servers) that store the one or more sets of instructions 220. The term "machine-readable media", as used here, also refers to any medium that is capable of storing, encoding or carrying a set of instructions 220 for execution by the computing device 200 and that cause the computing device 200 to perform any one or more of the methodologies of the present disclosure.

In some scenarios, the hardware entities 214 include an electronic circuit (e.g., a processor) programmed for facilitating the provision of a target map showing the location of a signal source. In this regard, it should be understood that the electronic circuit can access and run a surface masking application 224 installed on the computing device 200. The software application 224 is generally operative to: compute or obtain electrogram characteristic information 226 stored in memory 212; use the electrogram characteristic information 226 to generate a mask or modified mask to be overlayed on a surface for purposes of guiding movement of a sensor to locate a signal source; and/or cause the mask or modified mask to be displayed on the display 254 so as to be aligned with and overlayed on top of an image of an object or space in which the sensor is disposed. The mask may include, but is not limited to, a colored mask showing a probability of the source's presence in a given area of the object. This process can be iteratively performed until certain stop conditions are met (e.g., when a Total Conduction Delay ("TCD") divided by a Cycle Length ("CL") exceeds 0.7 and/or an unmasked area of the image is less than or equal to a threshold area value). Other functions of the software application 224 will become apparent as the discussion progresses.

The electrogram characteristic information 226 can specify at least one electrogram characteristic and/or include data that is useful for computing at least one electrogram characteristic. The electrogram characteristic can include, but is not limited to, a voltage, a First Activated Bipole ("FAB"), a TCD, a CL, and/or other time domain characteristic obtained from unipolar or bipolar electrogram signals recorded by an MPDC (e.g., last activated bipole, cycle width, etc.).

The electrogram characteristic information 226 can be acquired automatically, manually, or semi-automatically. In the automatic scenarios, an automated algorithm is employed to detect the cycles and calculate the electrogram characteristics. In the manual scenarios, a clinician may manually/visually find the electrogram characteristics and input them into the system via user-software interactions. The user-software interactions can involve indicating an electrogram characteristic on an electrogram plot and/or inputting electrogram characteristic values directly. In the semi-automatic scenarios, a combined manual and automatic algorithm is employed. For example, the clinician manually indicates the cycles on the electrogram plot using a virtual pen. The rest of the tasks (e.g., computation of the electrogram characteristics) can be performed automatically by using the cycles indicated by the clinician.

Notably, the electrogram characteristics are converted to meaningful information by the computing device 102. Hence, any other forms of input that can be converted to the required information, or an input of the required information itself directly can be considered within the scope of the present solution. For example, the FAB characteristic is converted to the direction of the wave by the computing device 102. Hence, any other input that can be converted to the wave direction can be used herein without limitation. TCD and CL are used herein as a convergence condition. Hence, any other input or algorithm that allows one to check for convergence (i.e., whether the current MPDC location is an AF source or not) can be used herein without limitation.

As noted above, the electrogram characteristic information 226 can include, but is not limited to, a CL, an FAB, and a TCD. CL, FAB and TCD are well known in the art, and therefore will not be described in detail herein. Still, a brief discussion of how these electrogram characteristics can be computed using an MPDC is now provided simply to assist the reader in fully understanding the present solution.

Figure 3:
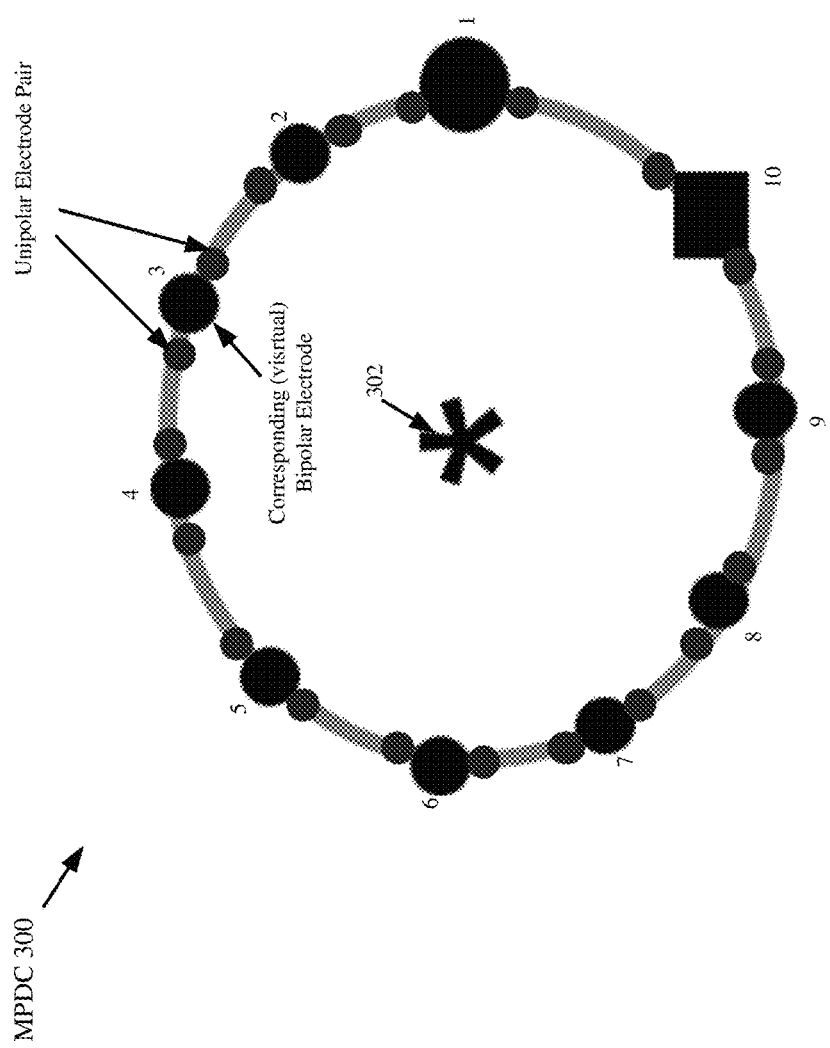
FIG. 3 provides an illustration of an exemplary electrode configuration for an MPDC in the system.

In order to understand how the electrogram characteristics are determined, an exemplary electrode configuration for an MPDC (e.g., MPDC 110 of FIG. 1) is explained with reference to FIG. 3. As shown in FIG. 3, a circular MPDC 300 comprises twenty (20) unipole electrodes that are arranged as pairs in a circular pattern such that the pairs are equally spaced for each other. Ten (10) bipole electrodes 1-10 are defined as mid-point positions of the unipole pairs as shown in FIG. 3 and equidistant from a center 302 of the MPDC. The electrogram signals generated by the unipole electrodes and/or bipole electrodes can be used herein to guide a sensor to locate a source of a propagating wave.

Figure 4:
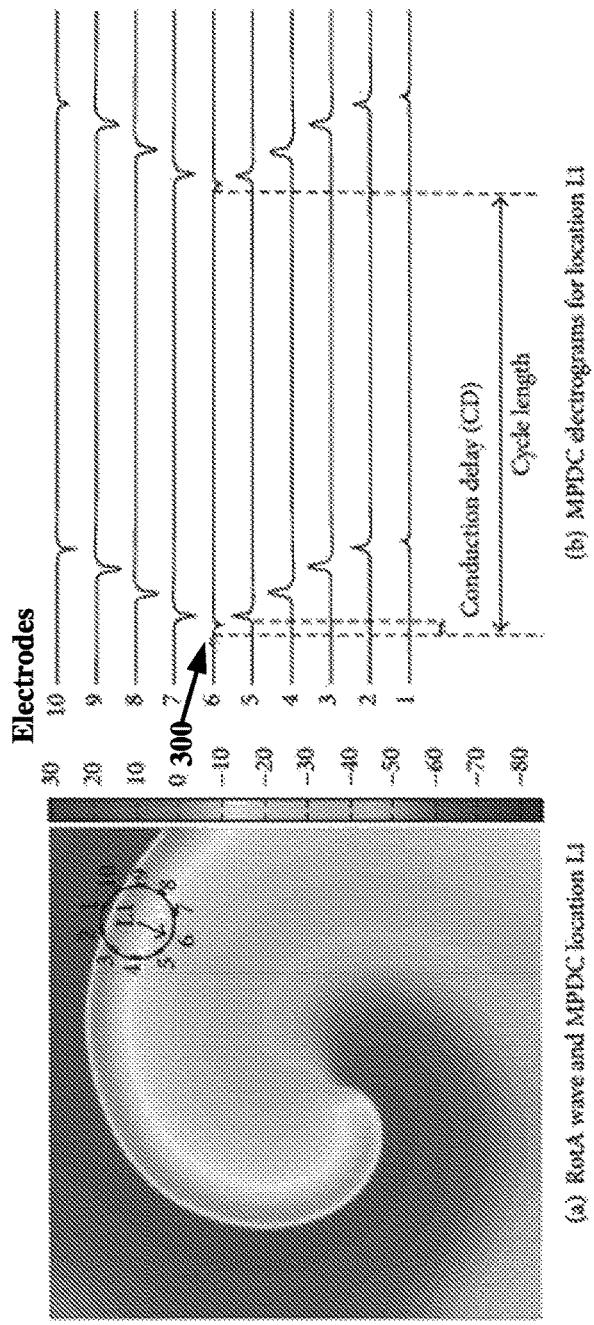
FIG. 4 provides graphs that are useful for understanding how electrogram characteristics can be determined based on electrogram sensor data acquired by electrodes of an MPDC.

Referring now to FIG. 4, there is provided graphs that are useful for understanding how electrogram characteristics can be determined based on electrogram sensor data acquired by the ten (10) bipole electrodes 1-10 of an MPDC (e.g., MPDC 110 of FIG. 1). The following electrogram characteristics can be determined at each recording site: FAB; TCD; and average CL at the FAB.

FAB is determined as the first bipole that encounters the wavefront (i.e., the bipole with the earliest activation time (AT)). The AT of each bipole is calculated with respect to the beginning of the recordings. For example, in FIG. 4(b), the FAB 300 implies that at MPDC location L1 the earliest activation occurred at bipole electrode 6 of the MPDC. The FAB is shown as the head of the arrow in FIG. 4(a).

The CD of a particular bipole electrode is calculated as the interval from each local activation to that of the next bipole electrode. For example, in FIG. 4(b), the CD of bipole electrode 5 ($CD_5$) is calculated as the time interval between the activations of bipole electrode 6 and bipole electrode 5. The CD of bipole electrode 4 ($CD_4$) is calculated with respect to bipole 5, and so forth. The $CD_1$ through $CD_9$ computations are obtained in accordance with the following Mathematical Equation (1).

$$CD_i = AT_{i+1} - AT_i \qquad (1)$$

Additionally, the CD of bipole electrode 10 ($CD_{10}$) is calculated as the time interval between bipole electrode 1 and bipole electrode 10 in accordance with the following Mathematical Equation (2).

$$CD_{10} = AT_1 - AT_{10} \qquad (2)$$

Figure 5:
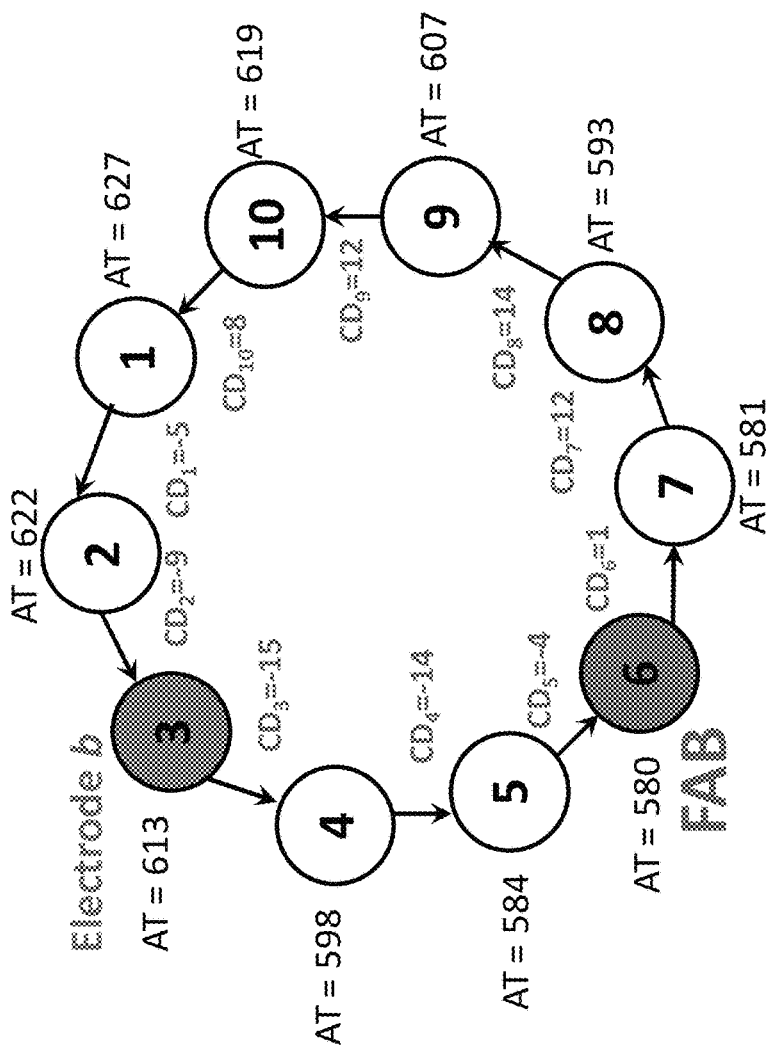
FIG. 5 provides a diagram that illustrates electrogram characteristics for an MPDC.

FIG. 5 illustrates how the CD and TCD calculations are performed for the MPDC in FIG. 4(b). Bipole electrode 6 is the FAB with the earliest activated time of 580 ms. $CD_1$ to $CD_{10}$ are calculated as explained above and shown for each bipole electrode. This procedure is continued for all cycles of the electrogram and the CD for every bipole electrode is averaged over the number of cycles to obtain a single value of CD for each electrode 1-10. Next, the electrode, b, with maximum absolute value CD was identified with the following Mathematical Equation (3)

$$b = \mathrm{argmax}(\{|CD_i|\}_{\{i=1:10\}}) \qquad (3)$$

In FIG. 4(b), b is electrode 3 with the largest absolute value CD. Finally, the summation of the average CD of every electrode is calculated to obtain the TCD at each recording site. The mathematical expression for TCD at any MPDC location (e.g., L1) is given by the following Mathematical Equation (4)

$$TCD = |\Sigma_{i=1}^{10} CD_i - CD_b| \qquad (4)$$

The CL is the time delay between two (2) successive activations in the same bipole electrode during consecutive cycles AT=607 (FIG. 3(b)). Here, CL is calculated as the average of the CL's for all of the bipole electrodes for a given MPDC location (e.g., L1). The CL of the FAB is calculated for different cycles and averaged over the number of cycles to obtain an average CL for the FAB.

Referring now to FIG. 6, there is provided a flow diagram of an exemplary method 600 for generating a target map. Notably, method 600 is described in relation to an atria based scenario. Method 600 is not limited in this regard, and can be used in any application where a target is to be localized using sensors. A person skilled in the art would readily understand how method 600 can be modified for other applications.

Figure 6A:
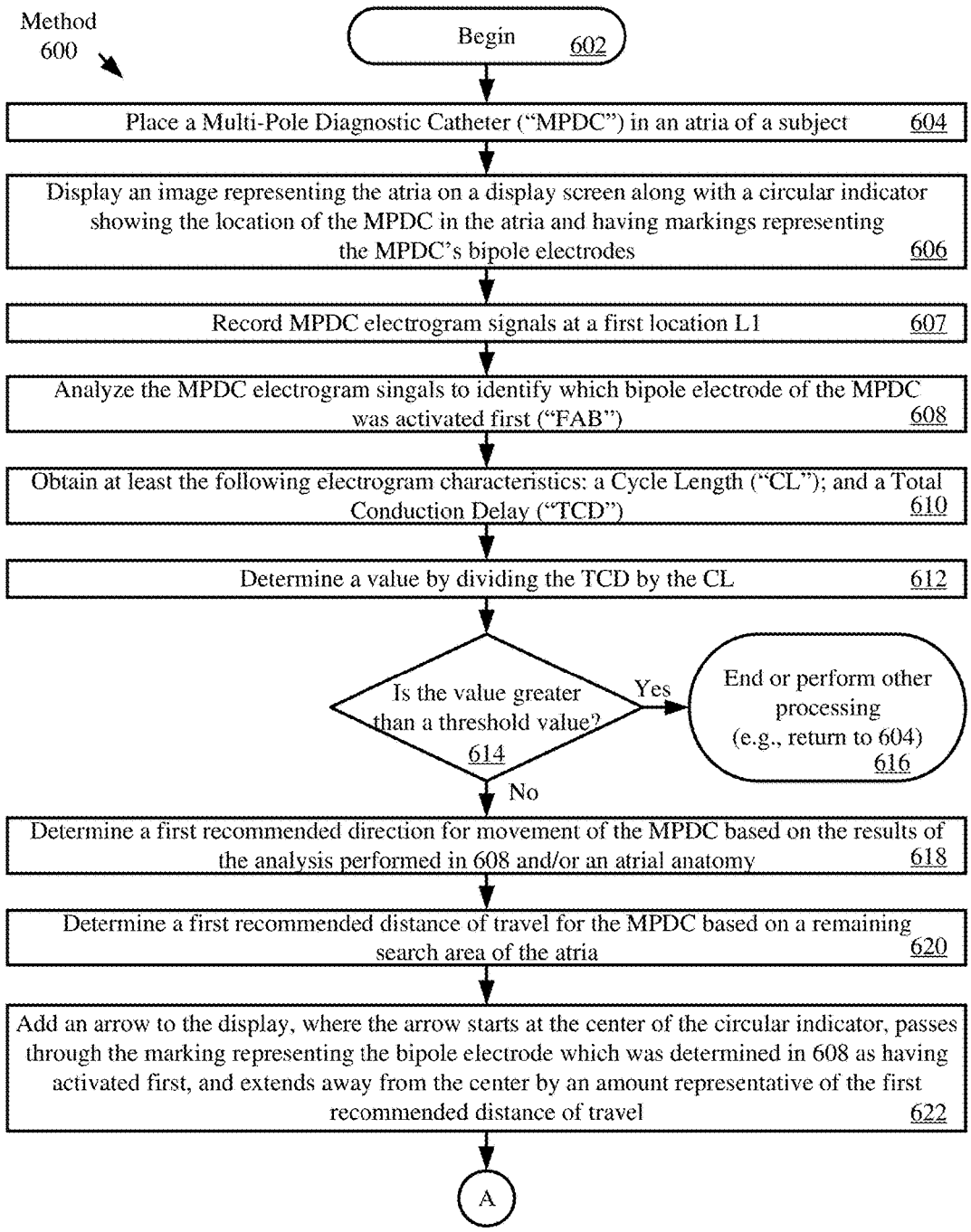
FIGS. 6(*a*)-6(*c*) (collectively referred to herein as "FIG. 6") provide a flow diagram of an exemplary method for localizing signal sources using multi-pole sensors.
Figure 7A:
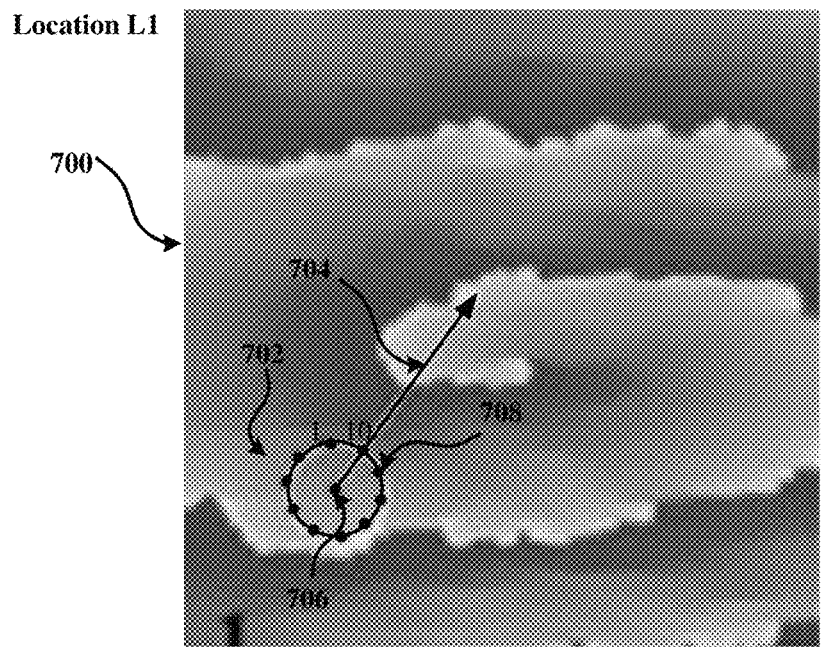
FIGS. 7(*a*)-7(*i*) (collectively referred to herein as "FIG. 7") provide a plurality of illustrations that are useful for understanding the method of FIG. 6.

As shown in FIG. 6A, method 600 begins with 602 and continues with 604 where an MPDC (e.g., MPDC 110 of FIG. 1) is placed in an atria of a subject (e.g., person 116 of FIG. 1). Next in 606, an image representing the atria (or a portion of the atria) is displayed on a display screen (e.g., display 254 of FIG. 2) of a computing device (e.g., computing device 102 of FIG. 1 and/or 200 of FIG. 2) along with a circular indicator showing the first location L1 of the MPDC in the atria. The circular indicator comprises a plurality of markings representing the MPDC's bipole electrodes. An exemplary sensed image 700 of human tissue showing a sensed rotor is provided in FIG. 7(a). FIG. 7(a) also shows an exemplary circular indicator 702 comprising a plurality of markings 708.

MPDC electrogram signals are recorded in 607 while the MPDC is at the first location L1. An illustration of ten (10) raw bipolar electrogram signals is provided in FIG. 7(b). Techniques for recording MPDC electrogram signals are well known in the art, and therefore will not be described herein. Any known or to be known technique for recording MPDC electrogram signals can be used herein without limitation. In some scenarios, this recording is achieved by communicating electrogram information (or data) to the computing device for subsequently processing during method 600.

Figure 7B:
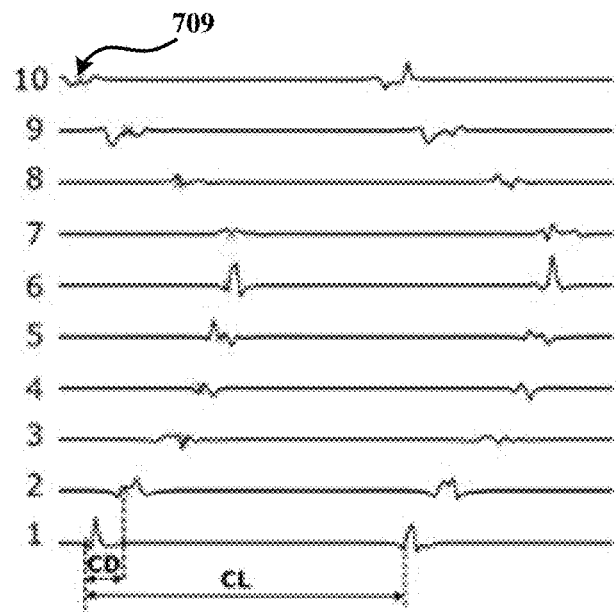
Figure 7C:
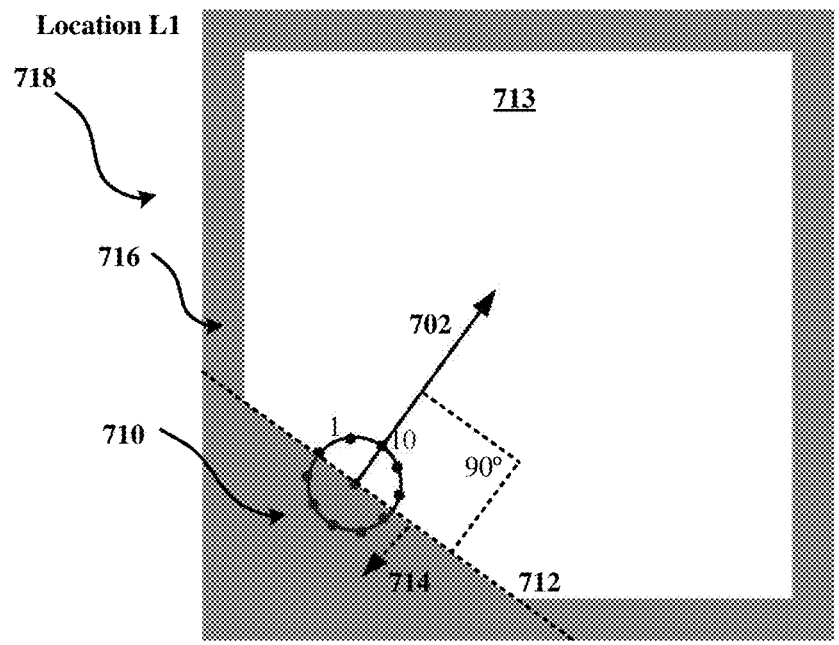
Figure 7D:
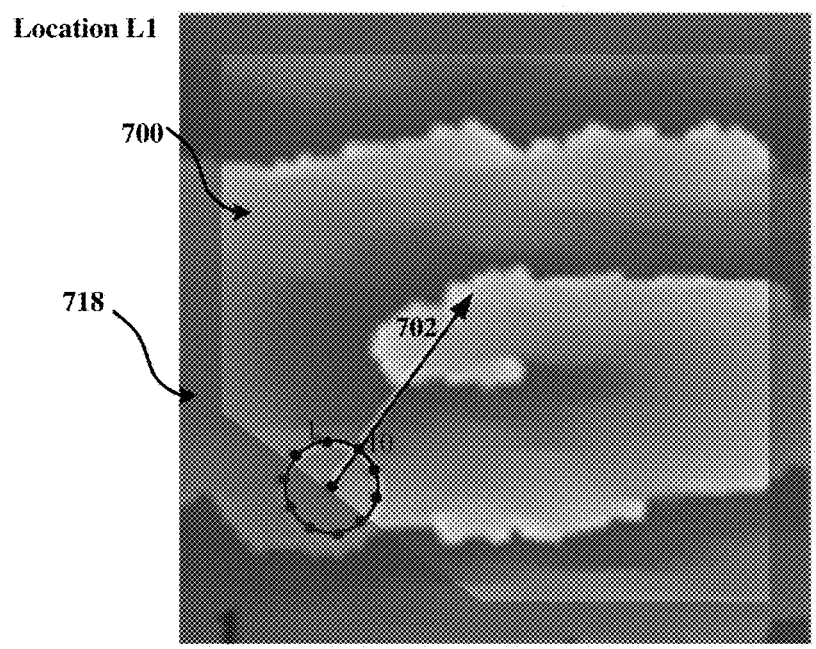
Figure 7E:
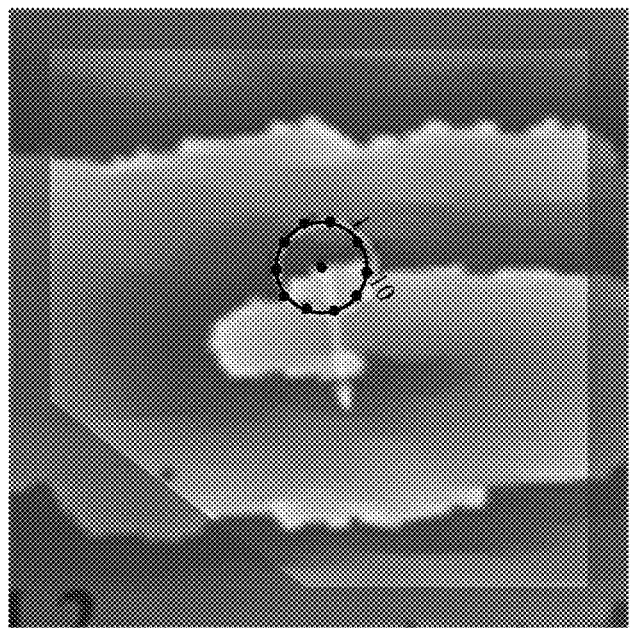
Figure 7F:
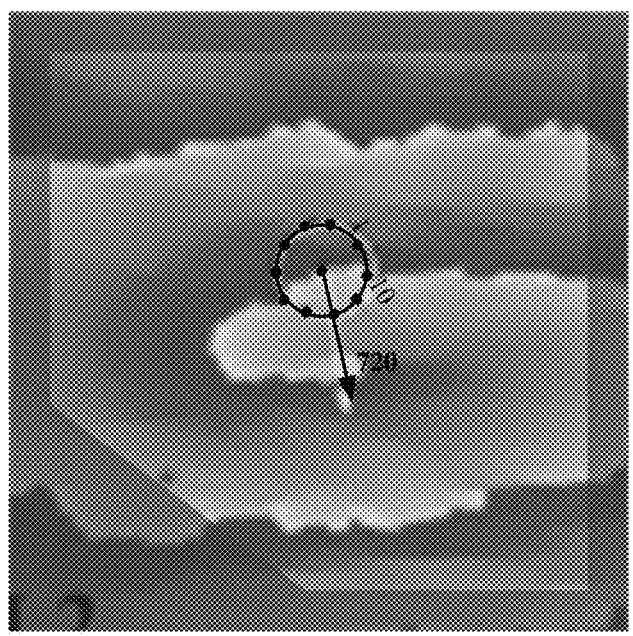
Figure 7G:
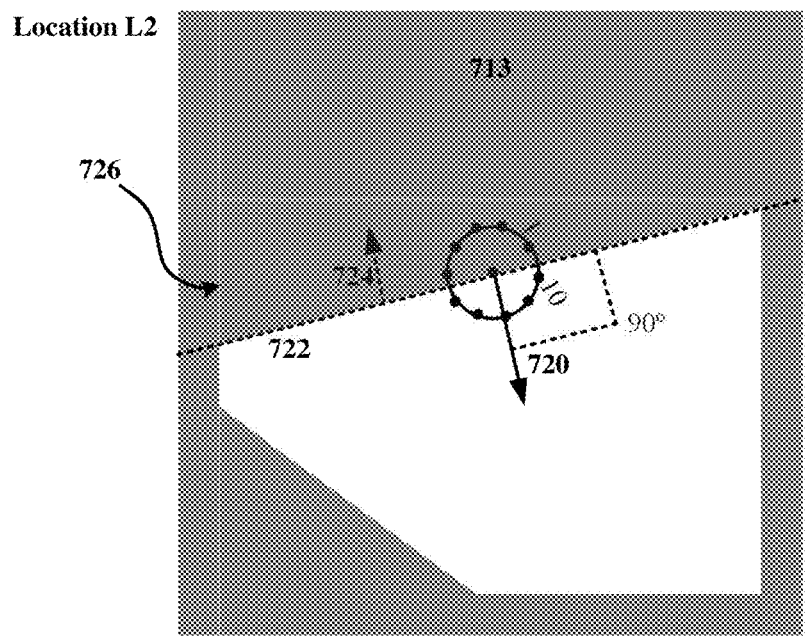
Figure 7H:
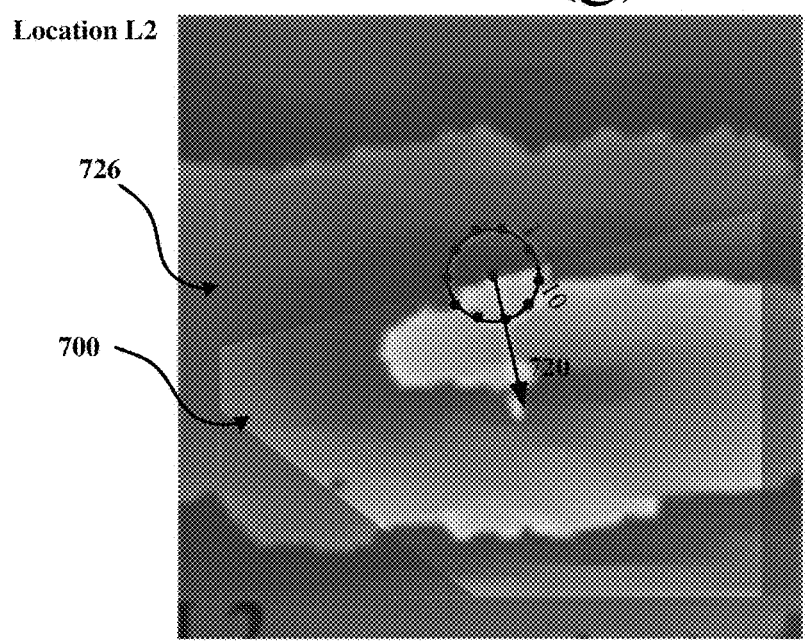
Figure 7I:
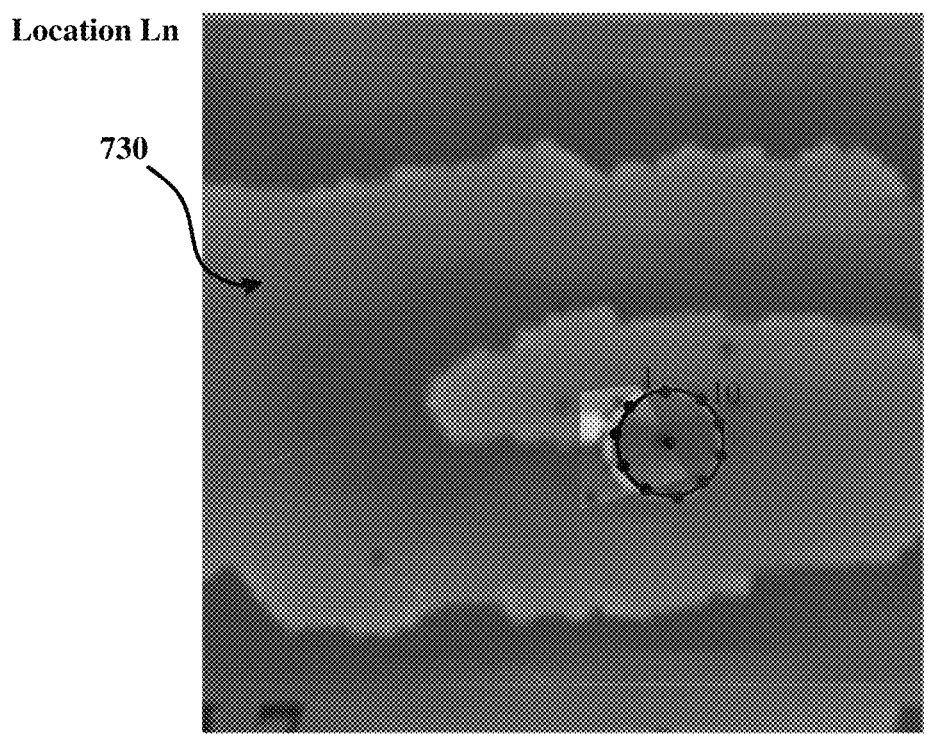

The MPDC electrogram signals are analyzed in 608 by the computing device to identify which bipole electrode (e.g., bipole electrode 10 of FIG. 3) of the MPDC was activated first by the propagating wave. The identified bipole electrode is considered an FAB. For example, the raw electrogram signals of FIG. 7(b) are analyzed to identify the raw electrogram signal with the first fluctuation 709 from a reference value (positive or negative) during a given period of time. The bipole electrode associated with the identified raw electrogram signal is determined to be the FAB. The present solution is not limited to the particulars of this example.

In 610, at least the following electrogram characteristics are obtained by the computing device: CL at the FAB; and a TCD. Techniques for obtaining electrogram characteristics are well known in the art. Any known or to be known technique can be used herein without limitation. Once the electrogram characteristics are obtained, the computing device performs the following computation in 612 to determine a value v.

$$v = TCD/CL$$

This value v is then used in 614 to determine if it is greater than a threshold value (e.g., 0.7). If the value v is greater than the threshold value (e.g., 0.7) [614:YES], then 616 is performed where method 600 ends or other processing is performed (e.g., return to 604). In contrast, if the value v is less than the threshold value (e.g., 0.7) [614:No], then 618-622 are performed.

618-620 involve: determining a first recommended direction for movement of the MPDC based on the results of the analysis performed in 608 and/or an atrial anatomy; and determining a first recommended distance of travel for the MPDC based on a remaining search area of the atria. The first recommended direction is defined by a line extending from a center of the MPDC to the FAB identified in 608 (e.g., bipole electrode 10 as shown in FIG. 7(a)). The first recommended distance of travel is defined as half the distance of the remaining search area of the atria. The search area can be acquired using imaging techniques (such as CT and/or MRI), mapping techniques (such as electroanatomic mapping), and/or any other virtual area obtained using the specifications of a subjects's atrium. The search area can be a 2D area transformed from a 3D coordinate system, a 3D surface (where the coordinates of the vertices of the surface are known or the equation of the 3D surface is known), and/or any other geometrical representation. The search area can be expressed in any domain—continuous, discrete, etc.

Next in 622, an arrow is added to the display showing the first recommended direction and distance of travel for the MPDC. An illustration of an exemplary arrow 704 that has been added to the display is provided in FIG. 7(*a*). Notably, the arrow 704 starts at the center 706 of the circular indicator, passes through the marking 708 representing the FAB (here bipole electrode 10), and extends away from the center 706 by an amount representative of the first recommended distance of travel.

Figure 6B:
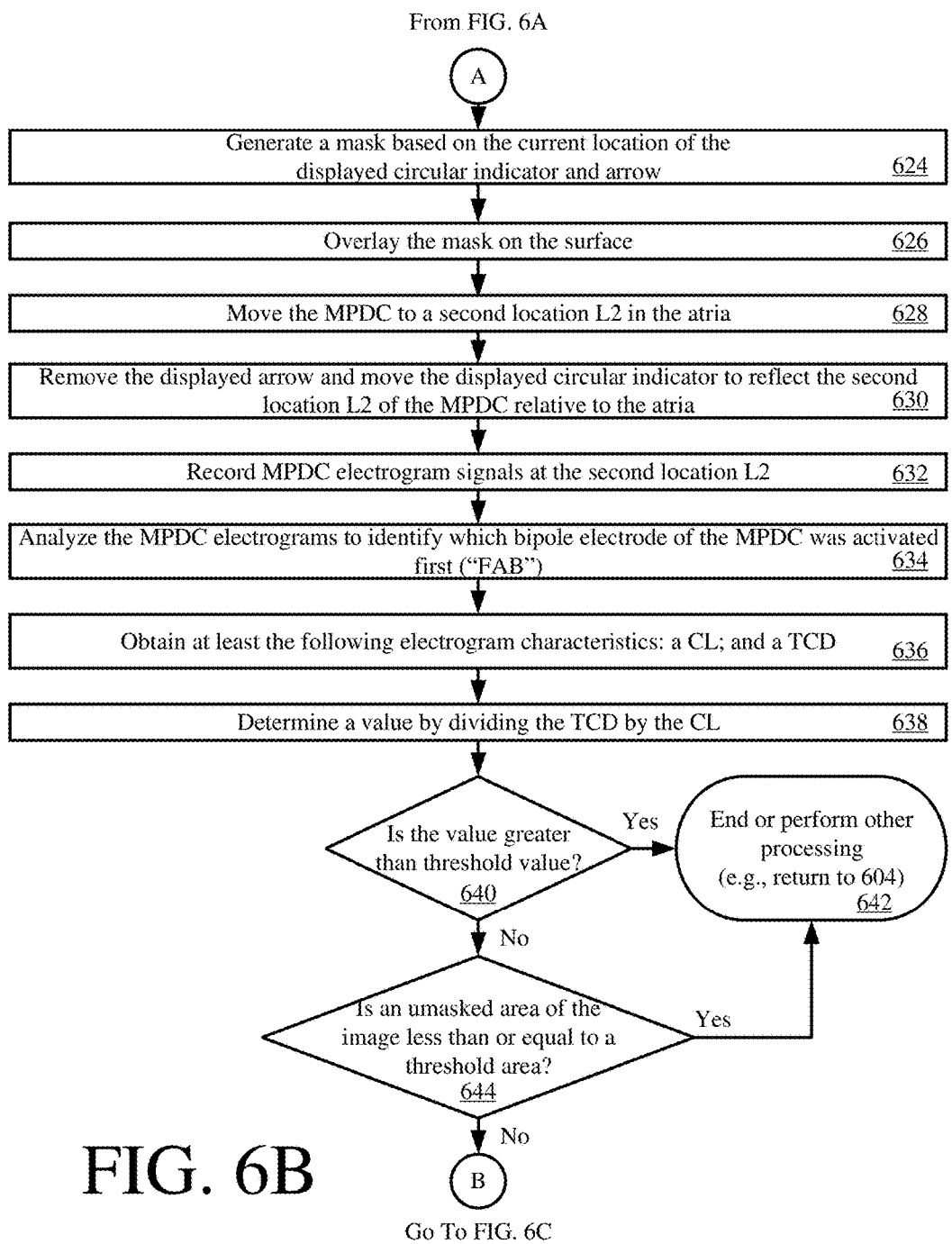

Upon completing 622, method 600 continues with 624 of FIG. 6B. As shown in FIG. 6B, 624 involves generating a mask based on the current location of the displayed circuit indicator and arrow. FIG. 7(*c*) provides an illustration that is useful for understanding how the mask is generated. As shown in FIG. 7(*b*), a line 712 is drawn that passes through the center 706 of the circuit indicator and is angled (e.g., less than or equal to ninety degrees (90°)) from the arrow 702. This line defines a boundary of the mask 718. The mask 718 covers the portion of a given area 713 that is in a direction 714 opposed from the direction defined by the arrow 702. The mask 718 may also comprise a portion of the area 713 which frames the same, as shown by 716. The present solution is not limited to the particulars of this example.

Referring again to FIG. 6B, the mask is then overlayed on the displayed surface image as shown by 626. An illustration of the mask 718 overlayed on the displayed image 700 is provided in FIG. 7(*d*). Upon completing 626, method 600 continues with 628.

628 involves moving the MPDC to a second location L2 in the atria. In response to this movement of the MPDC, the displayed arrow is removed and the displayed circular indicator is moved to reflect the second location L2 of the MPDC relative to the atria, as shown by 630. An illustration of a display with the arrow 702 removed therefrom and the circular indicator moved to reflect the MPDC's second location L2 is provided in FIG. 7(*e*).

MPDC unipolar electrogram signals are recorded in 632 while the MPDC is at the second location L2. The MPDC bipolar electrogram signals are computed and analyzed in 634 to identify which bipole electrode of the MPDC was activated first (e.g., bipole electrode 8 of FIG. 3) by the propagating wave. The identified bipole electrode is considered the FAB. The operations performed in 632 are the same as or similar to those performed in 608.

In 636, at least the following electrogram characteristics are obtained by the computing device: CL; and a TCD. The operations performed in 632 are the same as or similar to those performed in 610. Once the electrogram characteristics are obtained, the computing device performs a computation to determine a value v. This computation is discussed above in relation to 612.

Thereafter, decisions are made in 640 and 644 to determine if the mask needs to be modified in view of the MPDC electrogram signals recorded in 632. 640 involves determining if the value v is greater than a threshold value (e.g., 0.7). 644 involves determining if an unmasked area of the image is less than or equal to a threshold area. If the value v is greater than the threshold value [640:YES] and/or the unmasked area is less than or equal to the threshold area [644:YES], then 642 is performed where method 600 ends or other processing is performed (e.g., return to 604). In contrast, if the value v is less than the threshold value [640:NO] and the unmasked area is greater than the threshold area [644:NO], then method 600 continues with 644-646 of FIG. 6C.

Figure 6C:
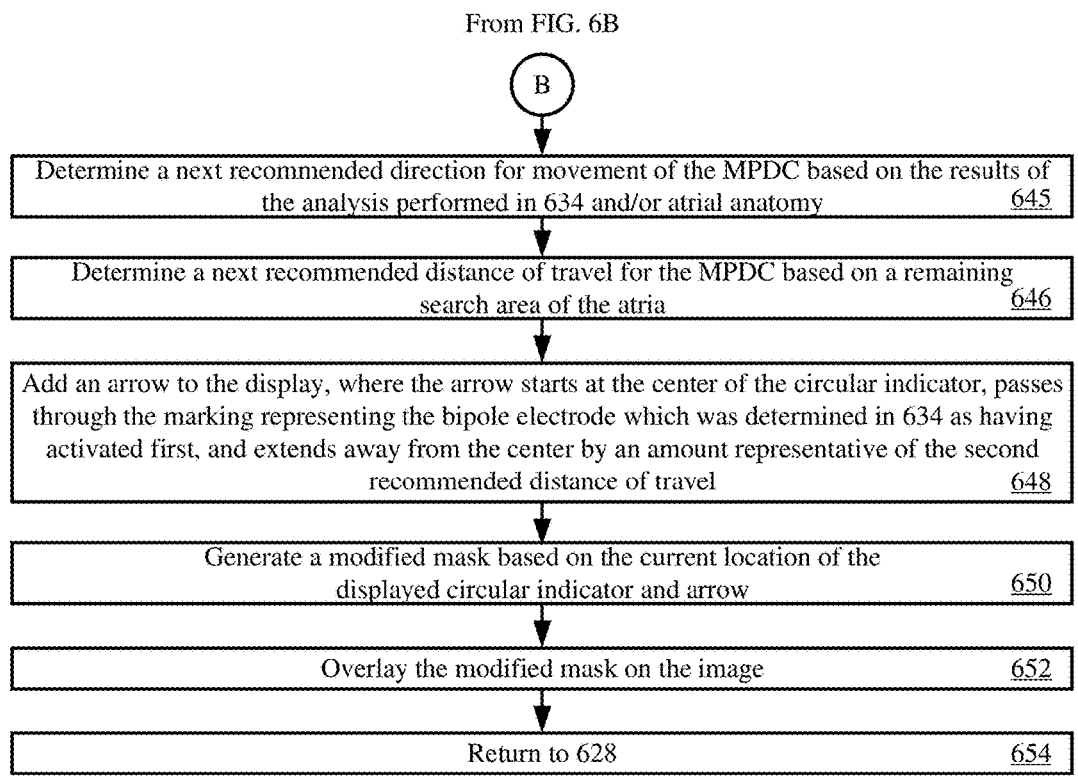

As shown in FIG. 6C, 645-646 involve: determining a second (or a next) recommended direction for movement of the MPDC based on the results of the analysis performed in 634 and/or atrial anatomy; and determining a second (or a next) recommended distance of travel for the MPDC based on a remaining search area of the atria. The second (or next) recommended direction is defined by a line extending from a center of the MPDC to the FAB identified in 634 (e.g., bipole electrode 8 as shown in FIG. 7(*f*)). The second (or next) recommended distance of travel is defined as half the distance of the remaining search area of the atria.

Next in 648, an arrow is added to the display showing the second (or next) recommended direction and distance of travel for the MPDC. An illustration of an exemplary arrow 720 that has been added to the display is provided in FIG. 7(*f*). Notably, the arrow 720 starts at the center 706 of the circular indicator, passes through the marking 708 representing the FAB (here bipole electrode 8), and extends away from the center 706 by an amount representative of the second (or next) recommended distance of travel.

Upon completing 648, 650 is performed by the computing device to generate a modified mask based on the current location of the displayed circuit indicator and arrow. FIG. 7(*g*) provides an illustration that is useful for understanding how the modified mask is generated in 650. As shown in FIG. 7(*g*), the mask 718 is used to generate the modified mask 726. A line 722 is drawn that passes through the center 706 of the circuit indicator and is angled (e.g., less than or equal to ninety degrees (90°)) from the arrow 720. This line defines a boundary of the modified mask 726. The modified mask 726 covers the additional portion of the given area 713 that is in a direction 724 opposed from the direction defined by the arrow 720. The present solution is not limited to the particulars of this example.

Referring again to FIG. 6C, the mask is then overlayed on the displayed image as shown by 652. An illustration of the modified mask 726 overlayed on the displayed image 700 is provided in FIG. 7(*h*). Upon completing 652, method 654 is performed where method 600 return to 628 so that the process can be iteratively performed until the value v is greater than the threshold value [640:YES] and/or the unmasked area is less than or equal to the threshold area [644:YES]. FIG. 7(*i*) provides an illustration of an exemplary final modified mask 730 overlayed on the displayed image 700.

Figure 8:
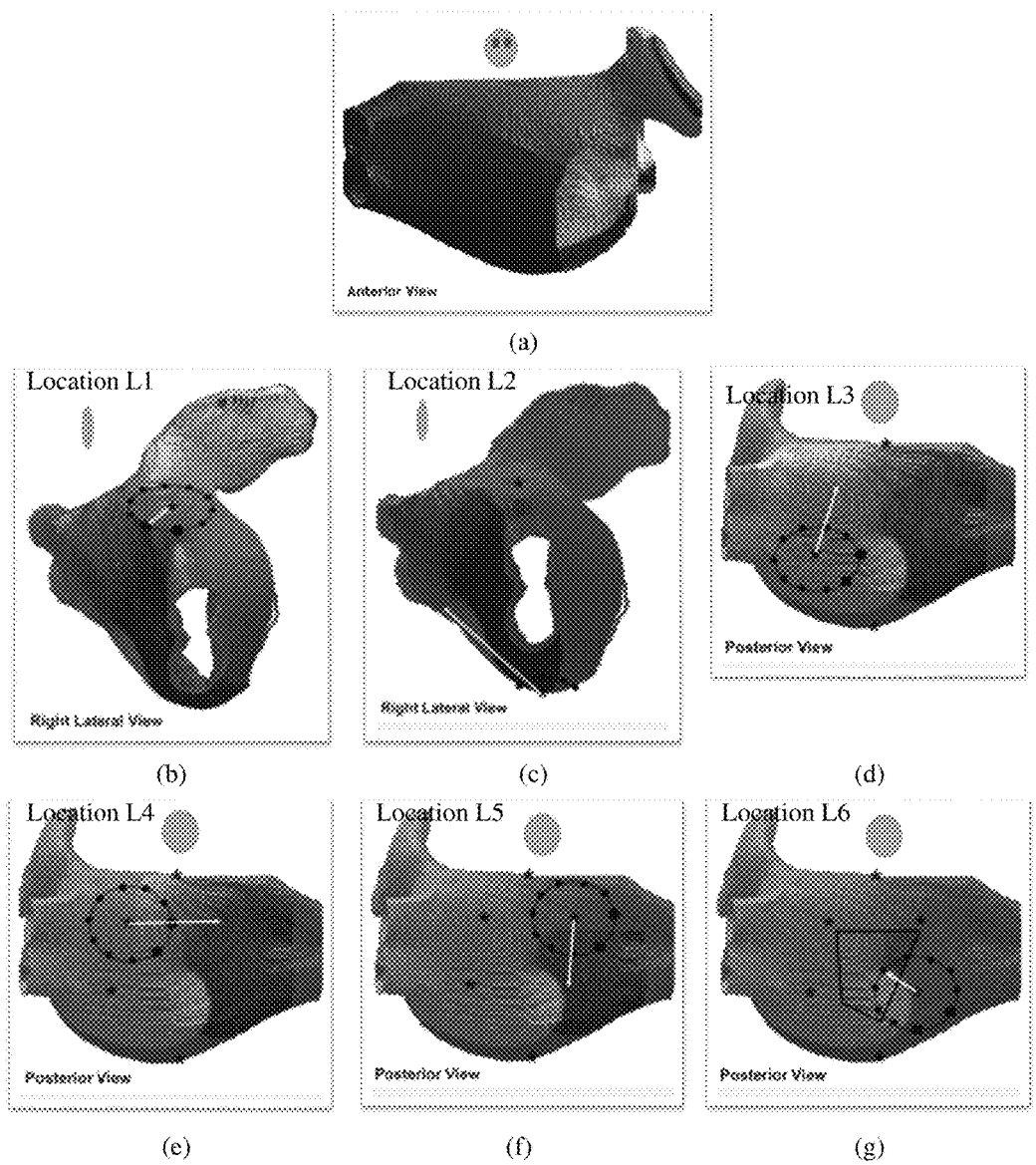
FIGS. 8(*a*)-8(*g*) (collectively referred to herein as "FIG. 8") provide a plurality of illustrations that are useful for understanding the present solution.

As noted above, the present solution is not limited to the particulars of the example shown in FIG. 7. For example, the present solution can be used in other applications in which the surface of the three dimensional images are masked for purposes of guiding an MPDC to a signal source (e.g., a source of rotor or repetitive focal). FIG. 8 provides illustration of such masked three dimensional images of an atria.

In view of the forgoing, the present solution generally concerns implementing systems and methods for guiding the movement of a sensor in an object or space. For example, in some scenarios, an MPDC is guided in an atria to develop an AF ablation target map. The ablation target map reveals the locations of any AF sources in the atria. The AF sources may include the propagating wave of bioelectricity that circulates in the tissue as a scroll wave or spiral (referred to as a rotor and shown in FIG. 7) or repetitive focal wave propagation (referred to as a foci). Characteristic(s) of recorded electrogram signals are used to decide on the location of the next movement of the MPDC. The present solution can be used in the left or right atrium depending on the clinical needs. The present solution is not limited to the particulars of this AF based example.

Figure 9:
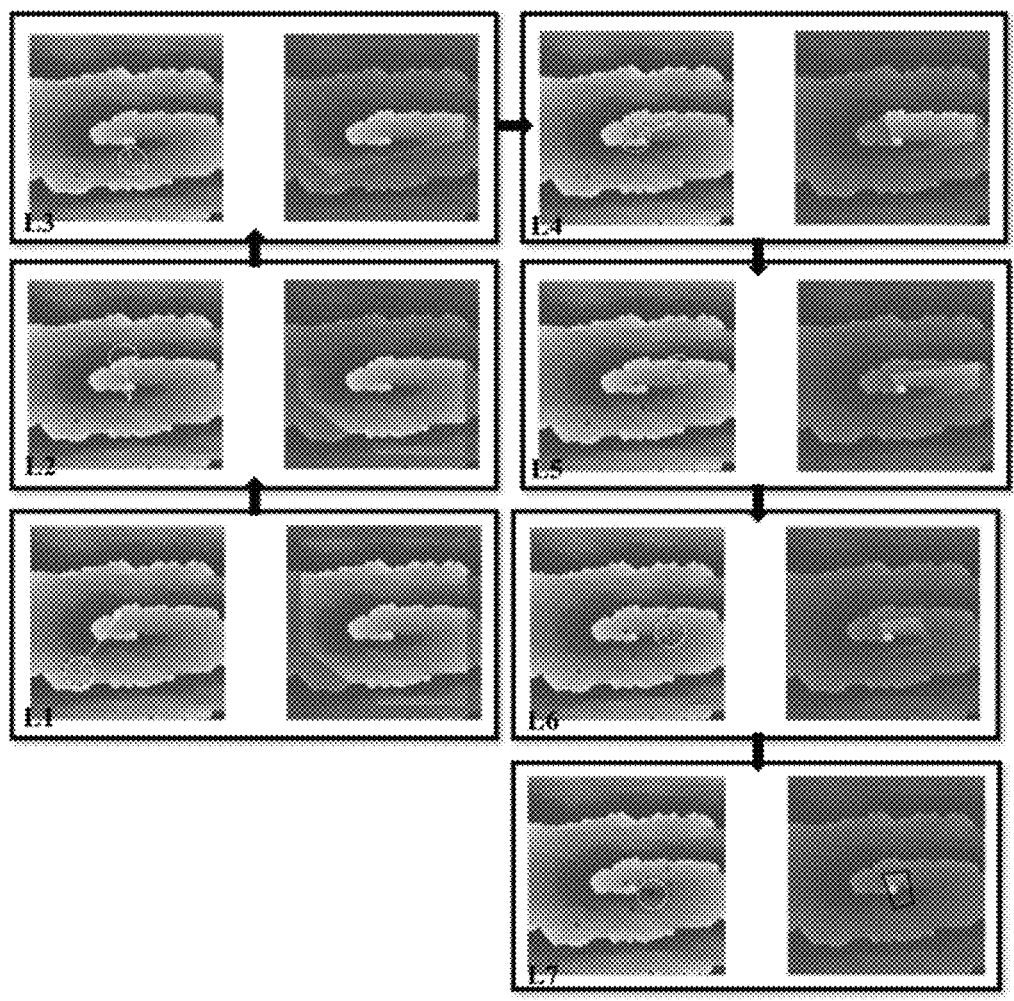
FIG. 9 provides an illustration showing a gradual update of an AF ablation target map and guidance of MPDC placements during a simulation.

To show the feasibility of the proposed solution, a 10 cm×10 cm heterogeneous human atrial tissue was simulated using an iconic model with collagenous septa (average length 2.5 mm) characteristic of fibrosis. The rotor meandering path was a circuit line approximately 1.5 cm long through the center of the tissue. A model was created of an MPDC with 20 unipole electrodes with a spacing of 4.5-1-4.5 mm (diameter of 15 mm) to obtain 10 bipole electrograms (see FIGS. 7(a) and 7(b)). The MPDC was placed in an arbitrary location on the atrial tissue. The present solution was used to guide the MPDC placement as it updated the AF ablation target map (in this case a rotor). The gradual update of the map and guidance of the MPDC placements (locations L2-L7) is shown in FIG. 9. The algorithm stopped at location L7 with a final AF ablation target map where the no-target region is shown in red and the delineated target region boundary is indicated in black.

The use of the present solution in MPDC applications has many advantages. For example in the MPDC application, the present solution is based on MPDC catheters (e.g., Lasso and/or Pentaray) that are routinely used in AF ablation procedures, and therefore does not require any specific equipment or type of catheter (such as basket catheters). As a result, the present solution will not enforce any additional risks or costs to the patients. Furthermore, MPDCs provide high resolution mapping of the atria and good quality of the electrogram recordings. Basket catheters have limited torque capabilities and limited maneuverability which hamper correct placement. Basket catheters can also abrade the endocardium.

The present solution provides a means to guide the placement of an MPDC in the atria to locate the AF sources (rotors and foci). Some conventional methods do involve an MPDC to detect the presence of an AF source in the atria, but they are based on random placements of the MPDC, i.e., there is no guidance of MPDC placement as is done in the present solution. As noted above, this guidance of MPDC placement is provided by the present solution via an AF ablation target map. The AF ablation target map provides a visual feedback for the clinicians in the electrophysiology laboratory as they perform an AF ablation procedure. The AF ablation target map can be used to delineate one AF source at a time or to delineate the regions of multiple AF sources at any given time. The type of AF source(s) (e.g., rotor, foci or other type) and/or the probability of an AF source at each delineated region may be provided along with the AF ablation target map. The AF ablation target map may be a 2D or 3D map which is quickly and effectively generated via the present solution.

The present solution may also be used in guiding of the ablation therapy in ventricular arrhythmias. In this case, a catheter is guided to locate reentrant or focal sources in ventricular tachycardia. In those or other scenarios, the present solution may use anatomic constraints of the heart to help guide the MPDC placement. For example, details about an atrium anatomy can be input into the computing device. These details can include, but are not limited to, the structure of the anatomy (e.g., left or right atrium), the structure or orientation of pulmonary veins, and/or the structure or orientation of an autonomic ganglia.

As noted above, the present solution provides a means for guiding a sensor placement. The guidance algorithm needs the following two inputs: direction; and distance. The direction and the distance can be produced by multiple techniques. For example, in FIG. 6, the FAB is used to give the direction and the search area is used to give the distance. The distance can additionally or alternatively comprise: a radius distance; a distance produced by a probabilistic (e.g., Likelihood methods) or Bayesian algorithm; a distance produced using a known/assumed model; a distance produced using a learned model (using parameter/machine learning approaches); an arbitrary distance value (such as half the maximum distance); and/or an estimated distance value.

In some scenarios, the guidance information of the system is represented on a target map as described above. Additionally or alternatively, the guidance information is represented on an anatomic map. For example, the guidance information is represented as: a sequential and final map (i.e., a visual target vs non-target map of the source region that gets updated with every move, and final delineated region of the source location); a pin pointed location map (another form of indication is to pinpoint the source location in the map, as opposed to a delineated region); a probabilistic map (i.e., a map illustrating the probability of an AF source being present at each location); and/or other visual representation of the source region or location.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

What is claimed is:

1. A method for guiding a sensor to locate a source of a propagating wave, comprising:

presenting, by a computing device, an electronic display comprising an image representing an object in which the sensor is placed and a visual indicator representing the sensor, the visual indicator positioned on the image so as to show a first location in the object at which the sensor currently resides;

receiving, by the computing device, a plurality of signals generated by a plurality of electrodes of the sensor while the sensor resides at the first location in the object;

determining, by the computing device, a first recommended direction of travel for the sensor based on the plurality of signals;

using, by the computing device, the first recommended direction of travel for the sensor to generate a mask that is to cover at least a portion of the image representing a portion of the object that is absent of the source;

modifying, by the computing device, the electronic display to include the mask overlaid on top of the image and an arrow showing the first recommended direction of travel for the sensor; and iteratively modifying the mask in accordance with sensor movement until (a) an unmasked area of the image is less than or equal to a threshold area or (b) a value exceeds a threshold value, where the value is computed by dividing a first signal characteristic by a second signal characteristic.

2. The method according to claim 1, wherein the determining further comprises:
analyzing, by the computing device, the plurality of signals to identify a first electrode of the plurality of electrodes which was activated first by the propagating wave; and
determining, by the computing device, the first recommended direction of travel for the sensor based on the position of the first electrode relative to a reference point on the sensor.

3. The method according to claim 1, wherein the mask comprises a colored mask showing a probability of the source's presence in a given area of the object.

4. The method according to claim 1, wherein the sensor comprises a Multi-Pole Diagnostic Catheter ("MPDC"), the propagating wave comprises a propagating wave of bioelectricity, and the plurality of signals comprise electrogram signals.

5. The method according to claim 4, wherein the object is an atria.

6. The method according to claim 1, further comprising:
determining a first recommended distance of travel for the sensor based on a remaining search area within the object; and
selecting a length of the arrow based on the first recommended distance of travel.

7. The method according to claim 1, wherein the visual indicator comprises a first marking representing the reference point and second markings respectively representing the electrodes, where adjacent ones of the second markings having a spacing illustrative of a spacing of adjacent ones of the electrodes.

8. The method according to claim 7, wherein the arrow starts at a center of the visual indicator, passes through the marking representing the first electrode, and extends away from the center of the visual indicator by an amount.

9. The method according to claim 8, wherein the mask is generated by:
drawing a line that passes through the center of the visual indicator, is angled ninety degrees relative to the arrow, and extends between first and second boundary lines of a space; and
defining a mask area as comprising a portion of the space that extends from the line in a direction opposed from the direction of the arrow.

10. The method according to claim 1, wherein the first signal characteristic comprises a Total Conduction Delay ("TCD") and the second signal characteristic comprises a Cycle Length ("CL").

11. The method according to claim 1, wherein the first direction of travel is determined based on the plurality of signals and an atrial anatomy.

12. A system, comprising:
a processor; and
a non-transitory computer-readable storage medium comprising programming instructions that are configured to cause the processor to implement a method for guiding a sensor to locate a source of a propagating wave, wherein the programming instructions comprise instructions to:
cause an electronic display to be presented that comprises an image representing an object in which the sensor is placed and a visual indicator representing the sensor, the visual indicator positioned on the image so as to show a first location in the object at which the sensor currently resides;
receive a plurality of signals generated by a plurality of electrodes of the sensor while the sensor resides at the first location in the object;
determine a first recommended direction of travel for the sensor based on the plurality of signals;
use the first recommended direction of travel for the sensor to generate a mask that is to cover at least a portion of the image representing a portion of the object that is absent of the source;
cause the electronic display to be modified so as to include the mask overlaid on top of the image and an arrow showing the first recommended direction of travel for the sensor; and
cause the mask to be iteratively modified in accordance with sensor movement until (a) an unmasked area of the image is less than or equal to a threshold area or (b) a value exceeds a threshold value, where the value is computed by dividing a first signal characteristic by a second signal characteristic.

13. The system according to claim 12, wherein the first recommended direction of travel is determined by:
analyzing the plurality of signals to identify a first electrode of the plurality of electrodes which was activated first by the propagating wave; and
determining the first recommended direction of travel for the sensor based on the position of the first electrode relative to a reference point on the sensor.

14. The system according to claim 12, wherein the mask comprises a colored mask showing a probability of the source's presence in a given area of the object.

15. The system according to claim 12, wherein the sensor comprises a Multi-Pole Diagnostic Catheter ("MPDC"), the propagating wave comprises a propagating wave of bioelectricity, and the plurality of signals comprise electrogram signals.

16. The system according to claim 14, wherein the object is an atria.

17. The system according to claim 12, wherein the programming instructions further comprise instructions to:
determine a first recommended distance of travel for the sensor based on a remaining search area within the object; and
select a length of the arrow based on the first recommended distance of travel.

18. The system according to claim 12, wherein the visual indicator comprises a first marking representing the reference point and second markings respectively representing the electrodes, where adjacent ones of the second markings having a spacing illustrative of a spacing of adjacent ones of the electrodes.

19. The system according to claim 18, wherein the arrow starts at a center of the visual indicator, passes through the marking representing the first electrode, and extends away from the center of the visual indicator by an amount.

20. The system according to claim 19, wherein the mask is generated by:
drawing a line that passes through the center of the visual indicator, is angled ninety degrees relative to the arrow, and extends between first and second boundary lines of a space; and
defining a mask area as comprising a portion of the space that extends from the line in a direction opposed from the direction of the arrow.

21. The system according to claim 12, wherein the first signal characteristic comprises a Total Conduction Delay ("TCD") and the second signal characteristic comprises a Cycle Length ("CL").

* * * * *